United States Patent
Thiem

(10) Patent No.: US 7,198,752 B2
(45) Date of Patent: Apr. 3, 2007

(54) DRIVE SYSTEM FOR AN APPARATUS FOR STAINING SPECIMENS

(75) Inventor: Stefan Thiem, Heidelberg (DE)

(73) Assignee: Leica Microsystems Nussloch GmbH, Nussloch (DE)

( * ) Notice: Subject to any disclaimer, the term of this patent is extended or adjusted under 35 U.S.C. 154(b) by 548 days.

(21) Appl. No.: 10/611,768

(22) Filed: Jul. 1, 2003

(65) Prior Publication Data

US 2004/0005244 A1 Jan. 8, 2004

(30) Foreign Application Priority Data

Jul. 5, 2002 (DE) ............................ 202 10 451 U

(51) Int. Cl.
- *G01N 33/00* (2006.01)
- *B65G 47/00* (2006.01)
- *B65G 37/00* (2006.01)
- *B65G 13/06* (2006.01)

(52) U.S. Cl. ............................ 422/63; 422/65; 422/66; 198/369.2; 198/608; 198/788; 198/789; 198/790; 198/791; 198/828; 198/838

(58) Field of Classification Search .................. 422/63, 422/65–67; 198/343.2, 369.2, 369.3, 371.2, 198/608, 666, 674, 788–791, 822, 824, 828, 198/835, 838

See application file for complete search history.

(56) References Cited

U.S. PATENT DOCUMENTS

| | | | |
|---|---|---|---|
| 1,919,169 A * | 7/1933 | Plausics | 198/369.2 |
| 3,428,027 A * | 2/1969 | Haen et al. | 119/57.6 |
| 3,691,988 A | 9/1972 | Clarke | |
| 4,152,390 A * | 5/1979 | Nosco et al. | 422/63 |
| 4,401,020 A * | 8/1983 | Brux | 100/7 |
| 4,756,399 A * | 7/1988 | Scata | 198/369.2 |
| 4,797,258 A * | 1/1989 | Mochida | 422/65 |
| 4,809,842 A * | 3/1989 | Aquino et al. | 198/369.2 |
| 4,861,553 A * | 8/1989 | Mawhirt et al. | 422/65 |
| 4,911,098 A | 3/1990 | Tabata | |
| 5,209,903 A * | 5/1993 | Kanamori et al. | 422/65 |
| 5,356,595 A * | 10/1994 | Kanamori et al. | 422/65 |
| 5,909,796 A * | 6/1999 | Soldavini | 198/369.2 |
| 6,074,617 A * | 6/2000 | DeYoung et al. | 422/104 |
| 6,227,376 B1 * | 5/2001 | Handel et al. | 209/606 |
| 6,355,487 B2 * | 3/2002 | Kowallis | 436/44 |
| 6,358,472 B1 * | 3/2002 | DeYoung et al. | 422/65 |
| 6,387,326 B1 * | 5/2002 | Edwards et al. | 422/63 |
| 6,555,062 B1 * | 4/2003 | Lewis et al. | 422/63 |
| 6,649,128 B1 * | 11/2003 | Meyer et al. | 422/63 |
| 2002/0104736 A1 * | 8/2002 | Peppel et al. | 198/369.2 |
| 2003/0087444 A1 * | 5/2003 | Chiou et al. | 436/47 |
| 2006/0013729 A1 * | 1/2006 | Carey et al. | 422/63 |
| 2006/0088443 A1 * | 4/2006 | Mattila et al. | 422/63 |

FOREIGN PATENT DOCUMENTS

| | | |
|---|---|---|
| DE | 41 17 833 C2 | 2/1992 |
| DE | 41 17 831 C2 | 12/1992 |

* cited by examiner

*Primary Examiner*—Brian R. Gordon
(74) *Attorney, Agent, or Firm*—Hodgson Russ LLP

(57) ABSTRACT

For automatic transportation and lifting and lowering of specimens in an automatic stainer, a drive system comprises a motor (16) and a side wall assembly (40), the motor (16) being coupled on the drive side to a first (12) and a second (14) crank system. The first (12) and second (14) crank systems are respectively coupled to the side wall assembly (40).

9 Claims, 3 Drawing Sheets

DRIVE SYSTEM FOR AN APPARATUS FOR STAINING SPECIMENS

CROSS REFERENCE TO RELATED APPLICATIONS

This application claims priority of the German utility model application 202 10 451.6 filed Jul. 5, 2002 which is incorporated by reference herein.

FIELD OF THE INVENTION

The invention concerns a drive system for an automatic stainer for staining specimens.

BACKGROUND OF THE INVENTION

In the microscopic examination of specimens, it is often necessary to mark certain parts or properties of the specimen by staining. In this way, for example, the structure in cells and tissues can be differentiated and made visible in high-contrast fashion. In order to emphasize structures selectively, it is necessary to adhere to certain staining procedures, called the "staining program," which depend on the particular preparations to be treated and the specific properties to be examined within the preparations. In practical use, a standard staining process has proven successful (in addition to various special stains) for this purpose. In this so-called H.E. staining process, the specimens pass through a number of processing stages using xylene, alcohol, eosin, hematoxylin, acetic acid, and water.

Since the staining process is often very time-consuming, it is advantageous to stain a large number of preparations in a single staining program or to automate the entire staining operation. In the staining of histological preparations for microscopic examinations, for example, the physical and chemical properties of the structures in the cells and tissues are utilized for the binding of certain dyes. Both natural substances and synthetic dyes are used for histological stains.

A number of types of automatic stainers, which automatically convey the specimens to the respective processing steps, are used for staining specimens. The automatic stainers differ in terms of their mechanical configuration and manner of operation.

DE 41 17 831 and DE 41 17 833 disclose several automatic staining methods and apparatuses. In an automatic stainer of the Mediate company, a specimen slide holder containing the specimen slides with histological preparations is transported into treatment stations located one behind another. The preparations are then lowered into a treatment station (called a "trough") and have applied to them an additional up-and-down motion that promotes complete staining. The motion mechanism of this device comprises two panels equipped with notches for receiving the specimens. One of these panels is located in front of the troughs and the other is located behind them. The two panels are each mounted on the frame of the device using a cross-type guide. A motor moves the panels, via a crank, in the vertical direction in order to extract the specimens from the reagent containers and lower them into the reagent containers. A second motor moves the specimens by way of a crank, when they have been extracted from the reagent containers, horizontally over the next reagent container. There they are lowered by a motion of the first motor. A third motor moves the panels, via a cam panel, vertically up and down in order to continuously mix the reagents. In this embodiment, two cross-type guides and three motors are required in order to perform the motions necessary for the staining process. The corresponding parts for motion transfer, and a number of sensors for each motor for position sensing, are additionally needed.

Also disclosed by the Shandon company is a staining device operating on the so-called carousel method. Here the treatment stations are arranged in a circle one behind another. The sequence in which the treatment stations can be traveled to is accordingly predefined.

U.S. Pat. No. 3,691,988 discloses a staining device for staining preparations that has a straight-line guide above the staining baths. A guide block that carries a number of preparations is arranged displaceably on this guide. That number of preparations is positioned by means of a chain drive, together with the guide block, over the desired staining bath and then lowered into the staining bath.

U.S. Pat. No. 4,911,098 additionally discloses an automatic staining apparatus that, using a gripper, can automatically lower into a staining bath a number of preparations that are to be stained. A tilting mechanism is provided for the gripper so that the chemical substances can easily drain off from the specimens being stained.

SUMMARY OF THE INVENTION

It is the object of the invention to propose an improved drive system for an automatic staining device, with which good staining results can be obtained even at high throughput rates.

According to the present invention, this object is achieved by way of a drive system for an automatic stainer comprising a motor (16); a side wall assembly (40) for carrying specimens to be stained; and a first crank system (12) and a second crank system (14) each coupled to the side wall assembly (40) and connected to the motor (16); wherein the motor (16) drives both the first and second crank systems (12, 14).

The drive system for an automatic stainer is thus characterized in that a motor is provided which is connected on the drive side to a first and a second crank system. The crank systems are in turn coupled to a side wall assembly of the automatic stainer that is designed to carry specimens. By way of this drive configuration, the first and the second crank system can be set in motion upon operation of the motor. Since the two crank systems are coupled to the side wall assembly, the motion of each of the crank systems is transferred to the side wall assembly. It is thus possible, using a single motor, to transfer to the side wall assembly of the automatic stainer a motion generated by the motor, different motion curves thereby being transferred via the two crank systems to the side wall assembly of the automatic stainer.

In a preferred embodiment, the two crank systems are mounted on a base frame of the automatic stainer. The crank systems each have a rotatably mounted shaft. Arranged at each of the end faces of the shafts are levers that extend parallel to one another. Each of the levers can have, at one of its ends, a rotatably mounted roller. The motor is advantageously arranged between the two crank systems, and on the drive side is in working engagement with the crank systems. The working engagement is preferably created by way of a toothed belt that runs from the motor respectively to the first and to the second crank system. With these two toothed belts, it is correspondingly possible to impose synchronous operation of the two crank systems.

To allow transport of the specimen preparations that are to be stained, there is provided on the automatic stainer a side wall assembly which has notches that are recessed, for example, into panels of the side wall assembly. The two panels are arranged parallel to one another and are joined rigidly to one another via transverse connections. At the two ends, each panel possesses a guide track. One of the crank systems can engage in each of these guide tracks, so that the motion of the crank system can be transferred to the frame. The guide track is preferably recessed into the frame by the fact that elements into which the guide track is recessed, in particular is milled, are attached onto the side wall assembly. Advantageously, these guide tracks have two surfaces that slope outward.

In a preferred embodiment of the invention, the rollers that are mounted rotatably on the cranks run in the guide tracks. Thus as soon as the motor begins to rotate, the rollers arranged and rotatably mounted at the ends of the cranks describe complete circles. Without additional actions, this complete-circle motion would of itself be transferred correspondingly to the side wall assembly. In order to lower the specimens that are present in the reagents vertically into the reagent containers and also pull them vertically back out, this complete-circle motion is trimmed. For that purpose, a gate is mounted rigidly on a base frame, and into it engages a peg that is attached to the side wall assembly.

With the use of the drive system according to the present invention, transport of the specimens in the automatic stainer can be accomplished using a single motor. The side wall assembly does not require a separate guide, since the drive mechanism that converts the rotary motion of the motor simultaneously provides guidance of the panels.

BRIEF DESCRIPTION OF THE DRAWINGS

Further advantages and advantageous embodiments of the invention are the subject matter of the Figures below and the descriptions thereof, in which true-to-scale reproduction has been dispensed with in the interest of clarity. Specifically.

DETAILED DESCRIPTION OF THE INVENTION

Figure 1:
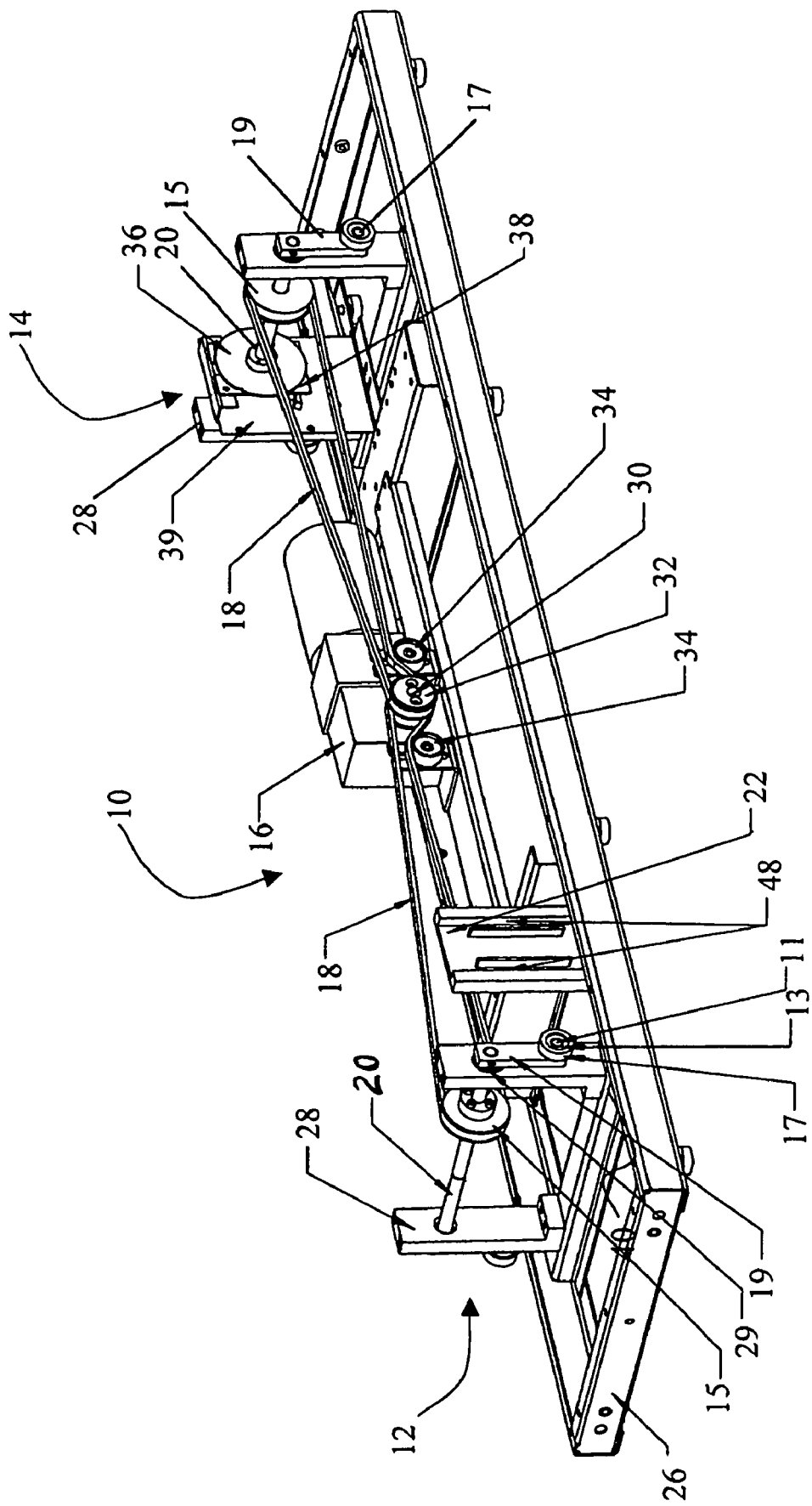
FIG. 1 is a perspective view of the drive system according to the present invention.

FIG. 1 shows the drive portion of an automatic stainer 10 in a perspective depiction. The drive system for automatic stainer 10 is implemented by way of a motor 16, a first crank system 12, and a second crank system 14. The two crank systems 12, 14 are connected to motor 16 on the drive side and are driven by toothed belts 18. The two crank systems 12, 14 are of substantially identical construction.

Four bearing blocks 28 are attached for this purpose on a base frame 26. Ball bearings 29 are pressed into bearing blocks 28. Two shafts 20 are mounted rotatably by means of ball bearings 29. Levers 19 are mounted rigidly on, in particular pressed onto, each of the ends of shafts 20. At the free ends of levers 19, a ball bearing 13, onto which a roller 17 is set, is provided on a pin 11.

Between bearing blocks 28, toothed-belt pulleys 15 are arranged on shafts 20. They are joined rigidly to the respective shaft 20. From toothed-belt pulleys 15, toothed belts 18 run toward motor 16. A double toothed pulley 32 that drives toothed belts 18 is mounted on motor shaft 30. Displaceable tension pulleys 34 can be provided for tensioning toothed belts 18. Mounted rigidly on shaft 20 of second crank system 14 is a coding disk 36 with which an angle code can be identified and thus the exact angular position of shaft 20 can be ascertained. For that purpose, coding disk 36 can have, for example, an imprinted code that can be read by sensors. These sensors can, for example, be arranged on a board 38 or associated with board 38. It is correspondingly possible, using this coding disk, to identify the respective present position of the entire transport mechanism, and thus to control the motion of the transport mechanism. Board 38 can, for example, be attached to base frame 26 using an angle bracket 39.

Figure 2:
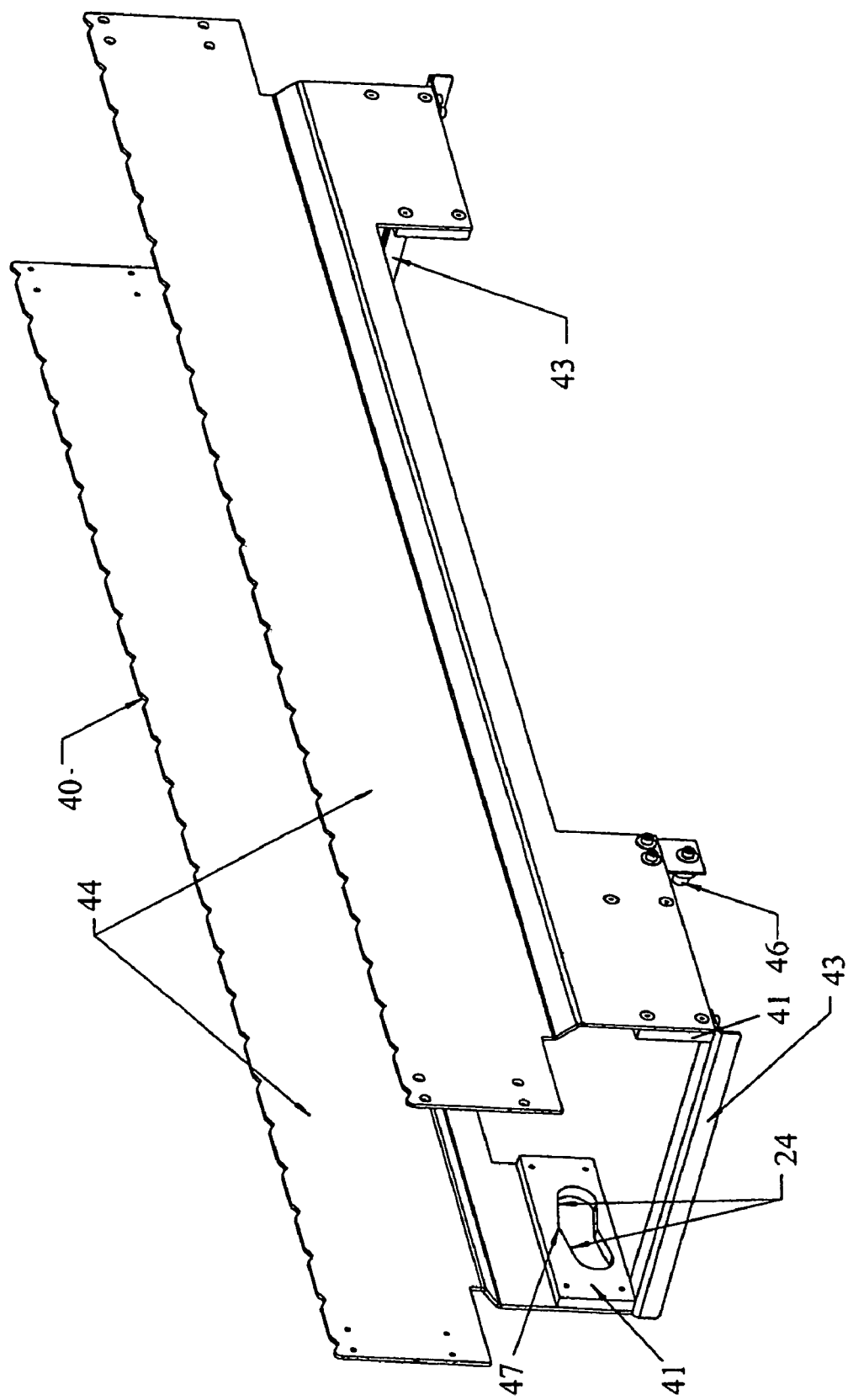
FIG. 2 shows a side wall assembly of the automatic stainer that can be coupled to the crank drive system.
Figure 3:
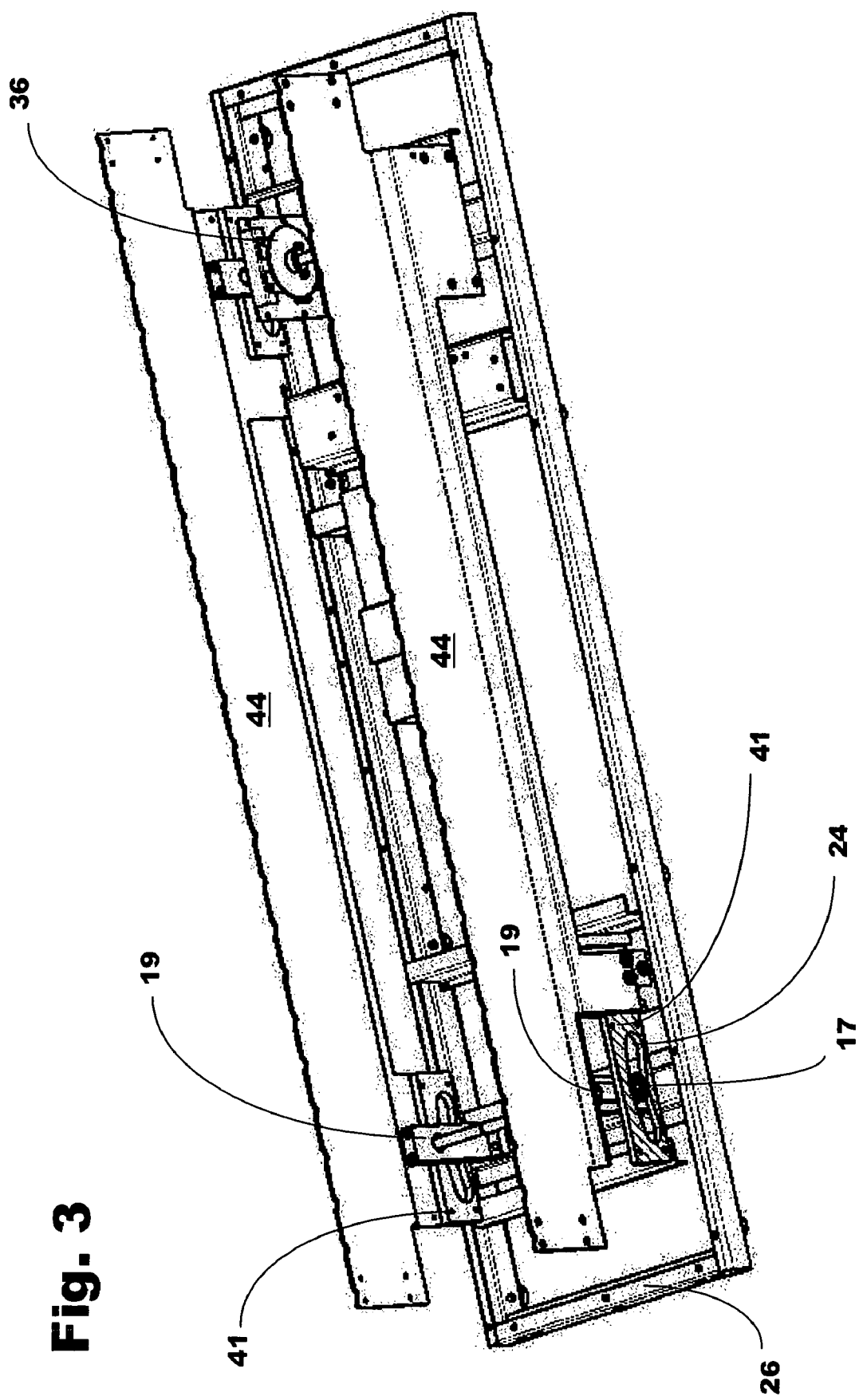
FIG. 3 is a perspective view showing the side wall assembly of FIG. 2 coupled to the drive system of FIG. 1.

FIG. 2 shows a side wall assembly 40 that can be coupled to the two crank systems 12, 14 as depicted in FIG. 3. Side wall assembly 40 has two panels 44 that form a lateral boundary of the side wall assembly. The two panels 44 are fixed in position with respect to one another at their long-side ends by transverse connectors 43 in such a way that they are aligned parallel. On each of panels 44, guide tracks 24 are provided at the two lower ends. Advantageously, these guide tracks are machined into so-called assembly elements 41 that are connected immovably to panels 44 and thus to side wall assembly 40. The assembly elements can be produced from any suitable material, in particular from sheet metal or a strong plastic. Guide track 24 extends in an outward-sloping fashion. As also depicted in FIG. 1, a gate 22 is additionally attached to base frame 26. Gate 22 possesses a milled-in gate guide track 24 in which a peg 46, attached to side wall assembly 40, can engage.

As soon as motor 16 is put into operation, the drive-side connection of motor 16 to first and second crank system 14, 14 causes levers 19 to be moved out of their lower position. Because of the connection of side wall assembly 40 to the drive system, side wall assembly 40 follows that motion until peg 46 comes to a stop against the outer boundary of gate guide track 48 of gate 22. At this point, panels 44 and therefore frame 40 are lifted vertically upward. Levers 19 continue to describe their circular path, and rollers 17 follow outward under guide track 24 of guide 41. Since guide track 24 is tilted outward, a horizontal force component is created which pushes pin 46 against the outer side of gate guide track 48. This prevents any horizontal motion of panels 44 during the lifting operation. As soon as roller 17 located on lever 19 approaches the upper reversing point of its circular motion, upper point 47 of guide track 24 snaps back onto roller 17. Side wall assembly 40 then once again follows the circular path of rollers 17 until pin 46 touches gate guide track 48 on the other side of gate 22. From that point on, side wall assembly 40 moves vertically downward.

PARTS LIST

10 Automatic stainer
11 Pin
12 First crank system
13 Ball bearing
14 Second crank system
15 Toothed-belt pulley
16 Motor
17 Roller
18 Toothed belt
19 Lever
20 Shaft
22 Gate
24 Guide track 26 Base frame
28 Bearing block
30 Motor shaft
32 Double toothed pulley
34 Tension pulleys
36 Coding disk
38 Board
39 Angle bracket
40 Side wall assembly
41 Assembly element
42 Guide
43 Transverse connector
44 Panel
46 Peg
47 Upper point
48 Gate guide track

What is claimed is:

1. A drive system for an automatic stainer (10), the drive system comprising:
    a motor (16);
    a side wall assembly (40) for carrying specimens to be stained; and
    a first crank system (12) and a second crank system (14) each coupled to the side wall assembly (40) and connected to the motor (16), wherein each of the first and second crank systems (12, 14) includes a rotatable mounted shaft (20) and a pair of levers (19) arranged one at each end of the shaft (20);
    wherein the motor (16) drives both the first and second crank systems (12, 14) and the first and second crank systems (12, 14) are each connected to the motor (16) by respective power transfer means for providing synchronized operation of the first and second crank systems (12, 14).

2. The drive system as defined in claim 1, wherein the power transfer means includes a toothed belt.

3. The drive system as defined in claim 1, further comprising a plurality of rollers (17) rotatably mounted one on each of the levers (19).

4. The drive system as defined in claim 3, wherein the side wall assembly (40) includes a plurality of sloped guide tracks (24) into which the plurality of rollers (17) engage, respectively.

5. The drive system as defined in claim 4, wherein the plurality of guide tracks (24) are respectively formed as recesses in an associated assembly element (41) mounted on the side wall assembly (40).

6. The drive system as defined in claim 5, wherein the side wall assembly (40) includes two panels (44) arranged opposite one another and a transverse connector (46) for joining the two panels (44) to one another.

7. An automatic stainer comprising:
    a base frame (26);
    a motor (16);
    a side wall assembly (40) for carrying specimens to be stained;
    a first crank system (12) and a second crank system (14) mounted on the base frame (26), each of the first and second crank systems (12, 14) being coupled to the side wall assembly (40) and connected to the motor (16);
    wherein the motor (16) drives both the first and second crank systems (12, 14); and
    a gate (22) fixed with respect to the base frame (26) and coupled to at least one of the first and second crank systems (12, 14).

8. The automatic stainer as defined in claim 7, wherein the gate (22) comprises a gate guide track (48), and the side wall assembly (40) includes a peg (46) arranged to engage the guide track (48).

9. The drive system as defined in claim 1, further comprising an angle sensor arranged to sense rotation of the shaft (20) of one of the first and second crank systems (12, 14).

* * * * *